(12) United States Patent
Webster (10) Patent No.: US 6,423,047 B1
(45) Date of Patent: Jul. 23, 2002

(54) DIAPERS

(76) Inventor: Patricia Mae Webster, 914 124th Pl. NW., Marysville, WA (US) 98271

( * ) Notice: Subject to any disclaimer, the term of this patent is extended or adjusted under 35 U.S.C. 154(b) by 127 days.

(21) Appl. No.: 09/595,406

(22) Filed: Jun. 16, 2000

(51) Int. Cl.[7] .................................................. A61F 13/15
(52) U.S. Cl. ............. 604/385.15; 604/378; 604/385.25; 604/385.26; 604/397
(58) Field of Search ................................. 604/374, 377, 604/396, 385.06, 385.09, 385.15, 385.26, 397, 378, 402, 385.08, 385.14, 385.25

(56) References Cited

U.S. PATENT DOCUMENTS

| | | | | |
|---|---|---|---|---|
| 4,230,113 A | * | 10/1980 | Mehta | 128/287 |
| 4,675,015 A | * | 6/1987 | Brown | 604/385 R |
| 4,769,023 A | * | 9/1988 | Goebel et al. | 604/385 R |
| 5,171,239 A | * | 12/1992 | Igaue et al. | 604/385.2 |
| 5,593,400 A | * | 1/1997 | O'Leary | 604/385.2 |
| 5,601,544 A | * | 2/1997 | Glaug et al. | 604/385.2 |
| 5,707,364 A | * | 1/1998 | Coates | 604/391 |
| 6,232,521 B1 | * | 5/2001 | Bewick-Sonntag et al. | 604/378 |

* cited by examiner

*Primary Examiner*—John G. Weiss
*Assistant Examiner*—Michael G. Bogart
(74) *Attorney, Agent, or Firm*—Kenneth W. Thomas (57) ABSTRACT

A reusable diaper product created to fit premature and newborn babies, toddlers, young youth, young adults, adults, the elderly, and patients with special problems such as a colostomy bag. The diaper comprises an all fabric stretchable shell which in the preferred embodiment is secured to the wearer by an encased elastic waistband with hook and loop VELCRO tabs. The legholes on the shell are encased elastic designed to fit many different leg sizes. Within the shell is disposed a soft breathable liquid impervious layer encasing multiple layers of a absorbent material. The sides of the absorbent material are permanently affixed to the shell and finished with elastic edges forming a body gusset of sorts. Several embodiments of the diaper are disclosed to fit special needs.

6 Claims, 10 Drawing Sheets

DIAPERS

The present invention relates to a comfortable reusable cloth diaper and the like, capable of being fitted to premature and newborn babies, babies, toddlers, young youth, young adults, and the elderly. Embodiments for special needs are disclosed.

BACKGROUND OF THE INVENTION

Historically the diaper has been a flat piece of cloth folded to a desired fit to contain bodily waste. Few substantial changes have been made over the years.

When disposable diapers came into being more absorbancy was required since users wore them for longer and longer periods of time. With the advent of environmental issues the reusable cloth diaper came upon the scene with a mass absorbtion problem and fitting of the wearer without pins.

At present there are two main types of diapers on the market for children, one a disposable diaper and two a reusable cloth diaper. However both of these diapers have an exterior impervious layer garment for prevention of leakage. In the case of the disposable diapers the impervious outer garment is attached to the interior absorbent layers and in the case of the reusable diaper the exterior impervious layer plastic garment is separate from the interior washable absorbent material and bodily shaped members. The exterior plastic garment creates an undesirable and distinct crackling sound. This is particularly undesirable when the reusable diaper is worn by an adult having for instance an incontinance health problem. Furthermore, the exterior plastic garment is normally a poor fitting and uncomfortable garment with some leakage problem.

SUMMARY AND OBJECTIVE OF THE INVENTION

By using the diaper of the present invention it is an objective to further enhance personal comfort with proper diapering and incontinent care. For ease of care the product entails an all in one complete unit with no pieces to put together with the added dignity of knowing what you are wearing can't be heard when moving. Namely, a diaper is provided comprising an outer liquid permeable material shell specifically a cloth shell shaped to fit the body. A continuous impervious layer of material is carried by the outer shell. Layers of absorbent material are disposed within and carried by said liquid impervious layer. The lifespan of the diaper is extended by utillizing a breathable liquid impervious fabric that will not crinkle or break in the washing and drying process. The diaper of the present invention is very soft and comfortable to the touch with the capabilities of naturally breaking down during the normal course of use even before it hits the landfills, yet capable of lasting through more than one sibling, therefor keeping overall cost, waste, and price down.

The use of birdseye absorbent material assures that comfort and breathability are achieved. The wearer needn't worry about the absorbent fabric keeping ones outer garment dry and it prevents extrements from staining the outer garment. Finally an outer cloth shell without being covered in plastic allows the air to come in contact with a greater portion of the skin, keeping a more healthy environment for the wearer.

In accordance with this invention the liquid impervious layer is completely covered in the waistband and leg area to ensure further comfort. A slight variation of size in the flannel lined VELCRO® sides attached to the outer shell allow maximum adjustments and still maintain a comfortable yet taut fit.

It is a great advantage that all the components are united as one with no pieces to put together and have the look and feel of underwear.

Another objective of this invention is the meeting of special needs without departing from the three main component system for the diaper.

BRIEF DESCRIPTION OF THE DRAWINGS

The present invention will be described in detail with reference to the accompanying drawings which illustrate a preferred embodiment of the invention and several other embodiments wherein.

DETAILED DESCRIPTION OF THE INVENTION

Figures 8, 8A:
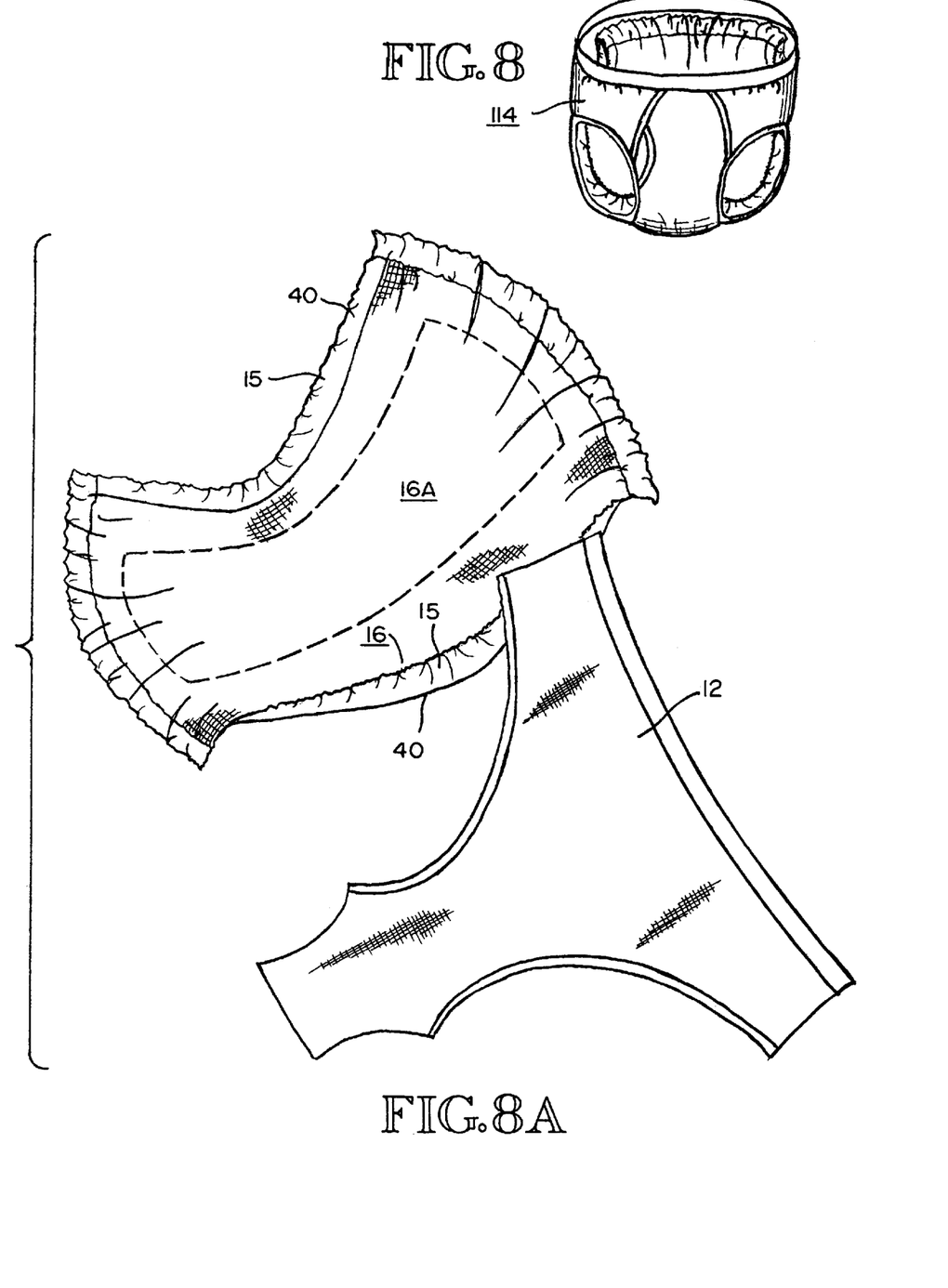
FIG. 8 shows an outer surface view of the boys/men pull-up diaper of the fifth embodiment of this invention and is shown in a position to be worn.
FIG. 8A is an interior surface view of the boys/men pull-up diaper in accordance with the fifth embodiment of this invention.
Figure 9:
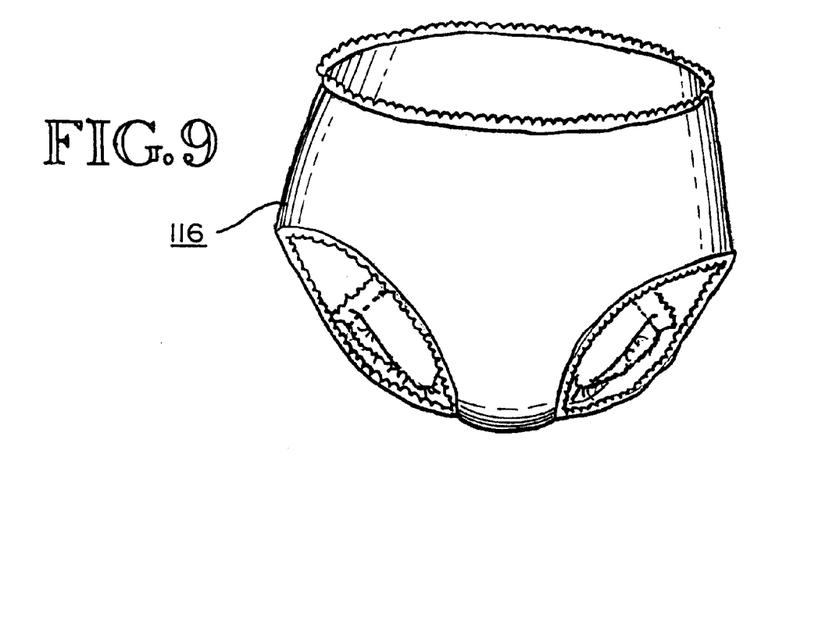
FIGS. 9 and 9A shows an outer surface view of the girls/women pull-up diaper of the fifth embodiment of this invention and is shown in a position to be worn.

FIGS. 1 through 4 illustrate a reusable diaper 10 made in accordance with the preferred embodiment of this invention in which various changes can be made to the diaper without departing from the spirit of the three main component system. As illustrated, the diaper 10 comprises an outer liquid permeable shell, specifically a cloth shell 12, having a back end 13 and a front end 14, and shaped to fit a body (not shown), a continuous liquid impervious layer 15, sewn to and carried by the cloth shell 12, and layers of absorbent liquid permeable material 16, having a central portion 16A, disposed within and sewn to and carried by the liquid impervious layer 15 with the liquid impervious layer 15 being of substantially the same general shape as the first layer 17 of absorbent material 16. The liquid impervious layer 15 is disposed between the cloth shell 12 and the absorbent material 16, and thus between the shell 12 and the central portion 16A of the absorbent material 16. Means 18, cooperating with the cloth shell 12, is provided for maintaining the positioning of the shell 12. However, it is to be understood that the shell 12 could be made from a liquid permeable material which would stretch to maintain the positioning of the shell 12 as shown in FIGS. 8 and 9.

Figure 1:
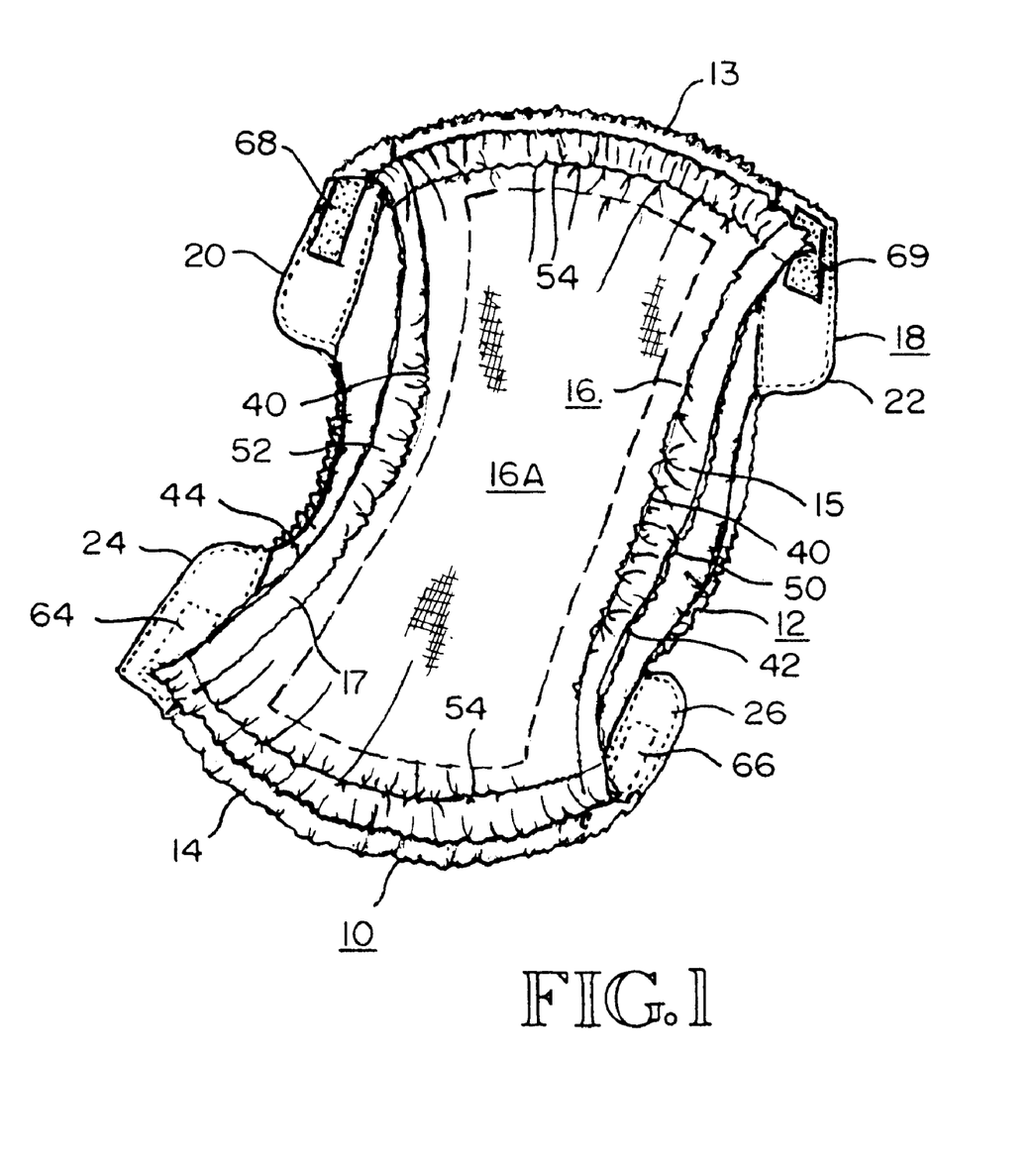
FIG. 1 is a perspective view of the preferred embodiment of a reusable diaper product made in accordance with the principles of this invention.
Figure 2:
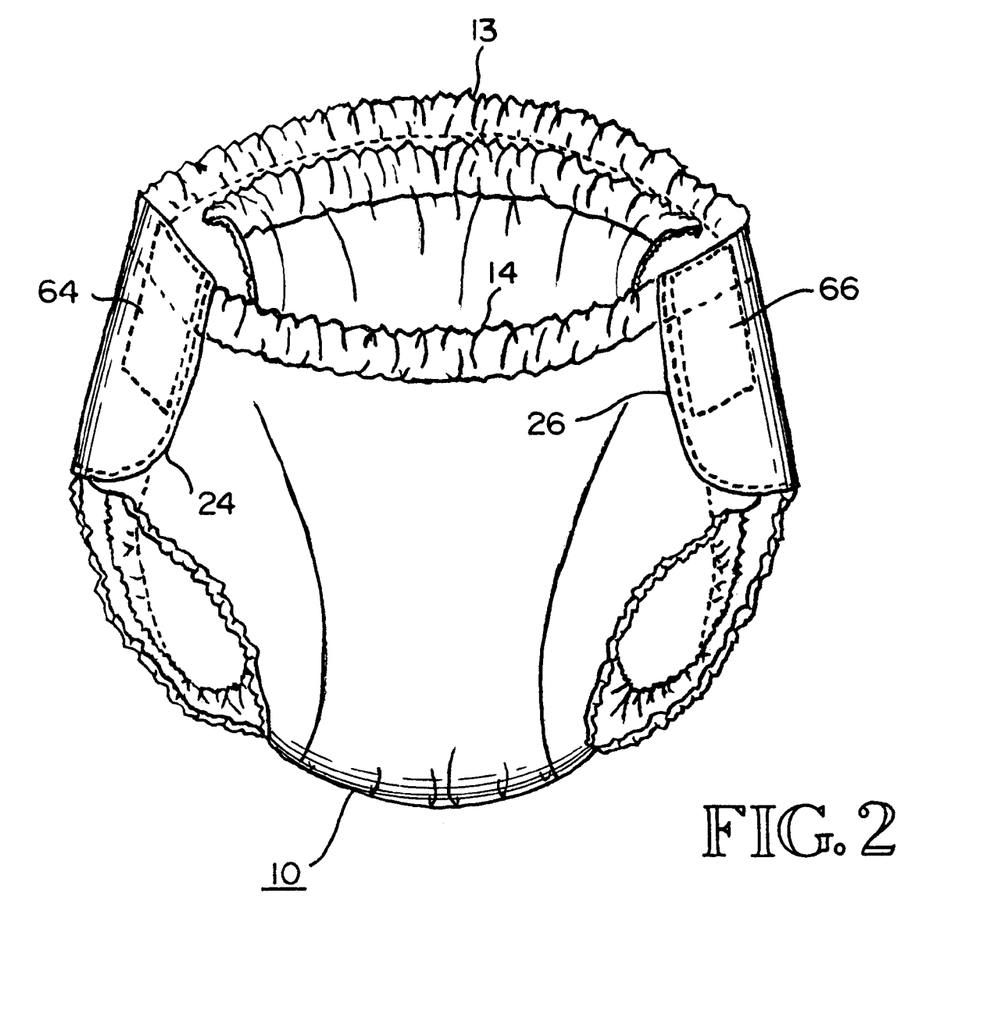
FIG. 2 shows a view of the preferred embodiment closed in a position for wearing.
Figure 3:
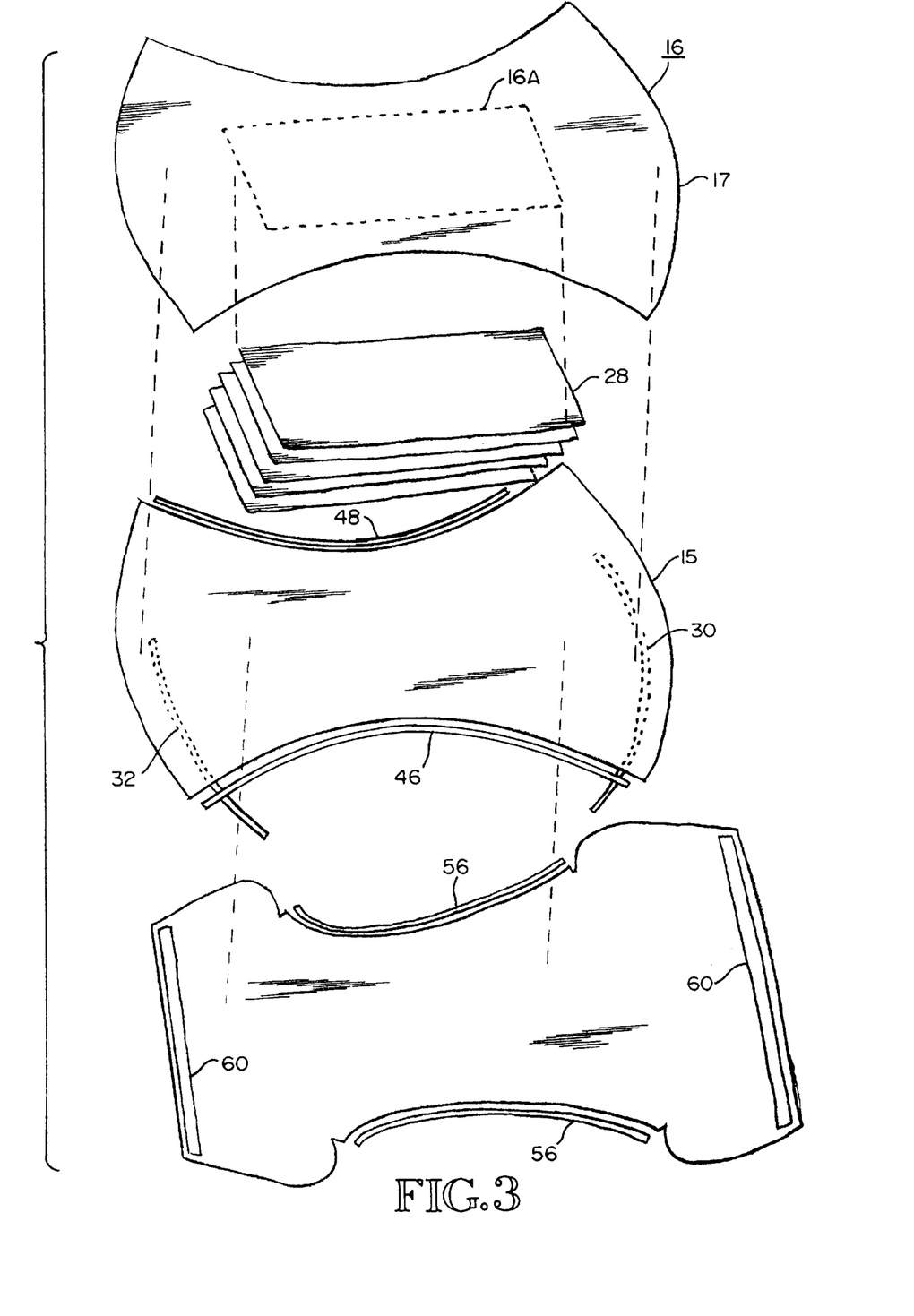
FIG. 3 illustrates the three main components of the preferred embodiment.
Figure 4:
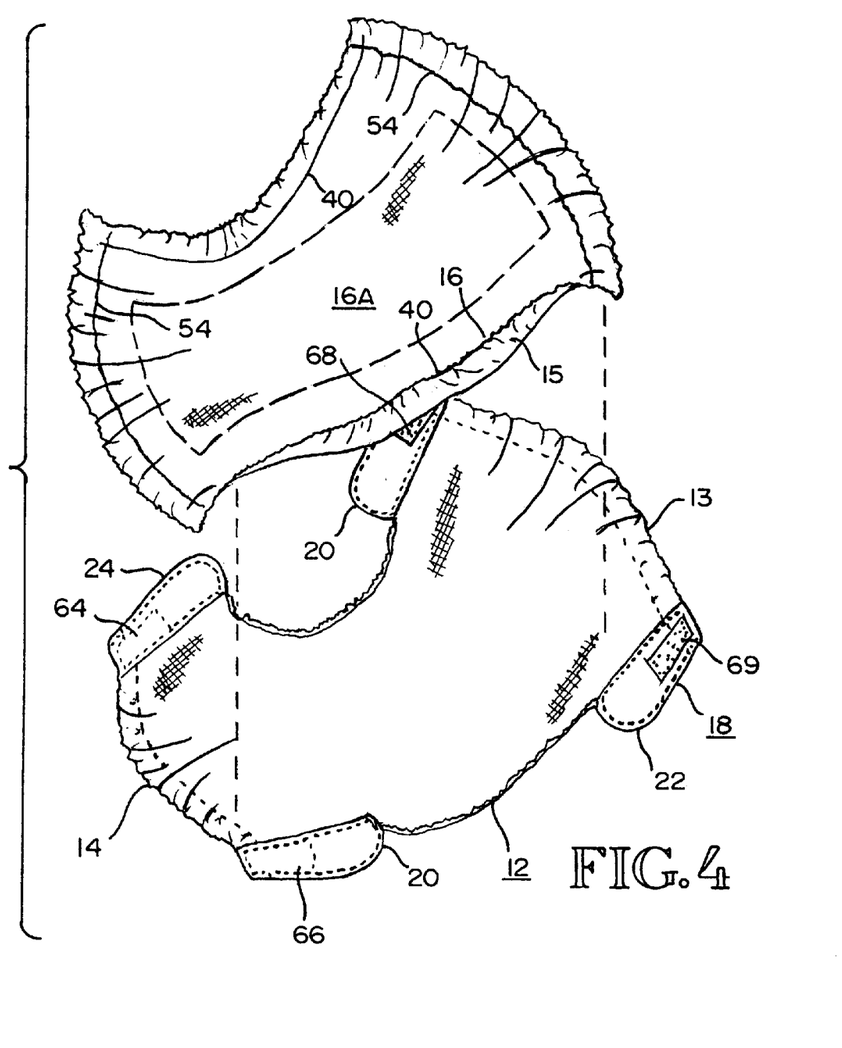
FIG. 4 illustrates the inner face of the preferred embodiment.
Figure 4A:
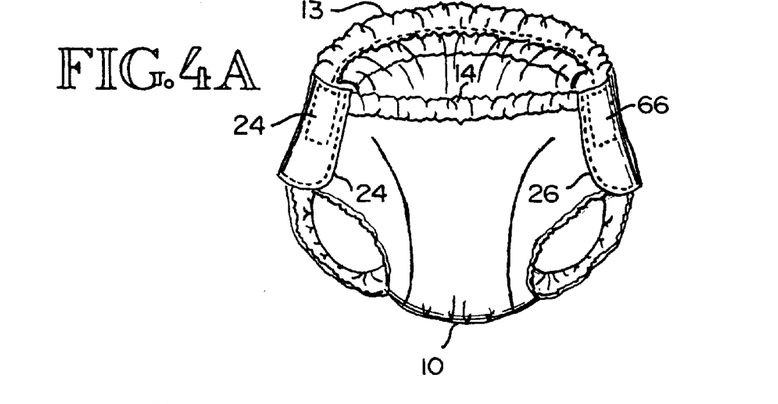
FIG. 4A shows an outside view of the preferred embodiment in a position to be worn.

As illustrated in FIGS. 3 and 4 the shell 12, is constructed of a stretchable liquid-permeable cloth fabric which may be cotten, knit, cotten blend, lycra, etc. Both back and front ends 13 & 14, respectively, of the shell 12 are substantially identical in shape although the back side 13 will be slightly larger. Extended from each corner of the shell 12 are tabs 20, 22 24, and 26. Each tab 20, 22 24 and 26 is covered on the inside with flannel material, the tab is then turned and topstitched.

The liquid impervious layer 15 is preferrably a polyester vinyl coated material and is generally of the same shape as the first layer 17 of absorbent material 16. Five elongated shaped absorbent layers 28 of, for instance, birdseye fabric are centered and stitched to the first layer 17 of absorbent material 16, which also may be birdseye fabric to form the central portion 16A which includes a portion of the layer 17. The size and number of layers 28 varies with the amount of absorbentsy desired. Pieces of elastic 30 and 32 gathers the first layer of absorbent material 17 and the impervious layer 15 at the stitching line 54 just off horizontal edges to fit different shell sizes.

All of the absorbent layers 28 are retained together with a finishing serged edge and sewn to the first absorbent layer 17. The first absorbent layer 17 and the liquid impervious layer 15 are retained together with a finishing serged edge and are permanently attached to the shell 12 by lines of stitching 40 just off the vertical edges 42 and 44, respectively, of the first absorbent layer 17 to create leg gussets 50 and 52. Elastic 46 and 48 is also serged to the vertical edges 42 and 44. Lines of stitching 54 hold the elastic 30 and 32 on the liquid impervious layer 15 and attach the liquid impervious layer 15 to the first layer 17 of absorbent material 16. Although not preferred the central portion 16A of the absorbent material 16 could extend between the stitching lines 40—40 and 54—54.

Elastic 56 is serged to leg holes on the shell 12 turned and topstitched. Elastic 60 is also serged to the waistband area on the front 14 and back 13 of the shell 12, turned and topstitched. In order to secure the front 14 of the shell 12 to the back 13 of the shell 12 and thus hold the diaper 10 up, VELCRO® hooks 64 and 66 are placed on the tabs 24 and 26 on the front 14 of the shell 12 and corresponding VELCRO® loops 68 and 69 are placed on the tabs 20 and 22, respectively, of the back 13 of the shell 12.

Figure 5:
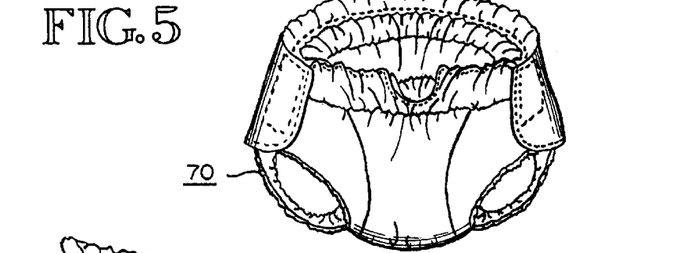
FIG. 5 is a view of the premature or newborn baby diaper in a worn position in accordance with a second embodiment of this invention.

FIG. 5 is a front view of a diaper 70 folded in a position to be worn by a premature or newborn baby and constructed in accordance with the second embodiment of this invention.

Figure 5A:
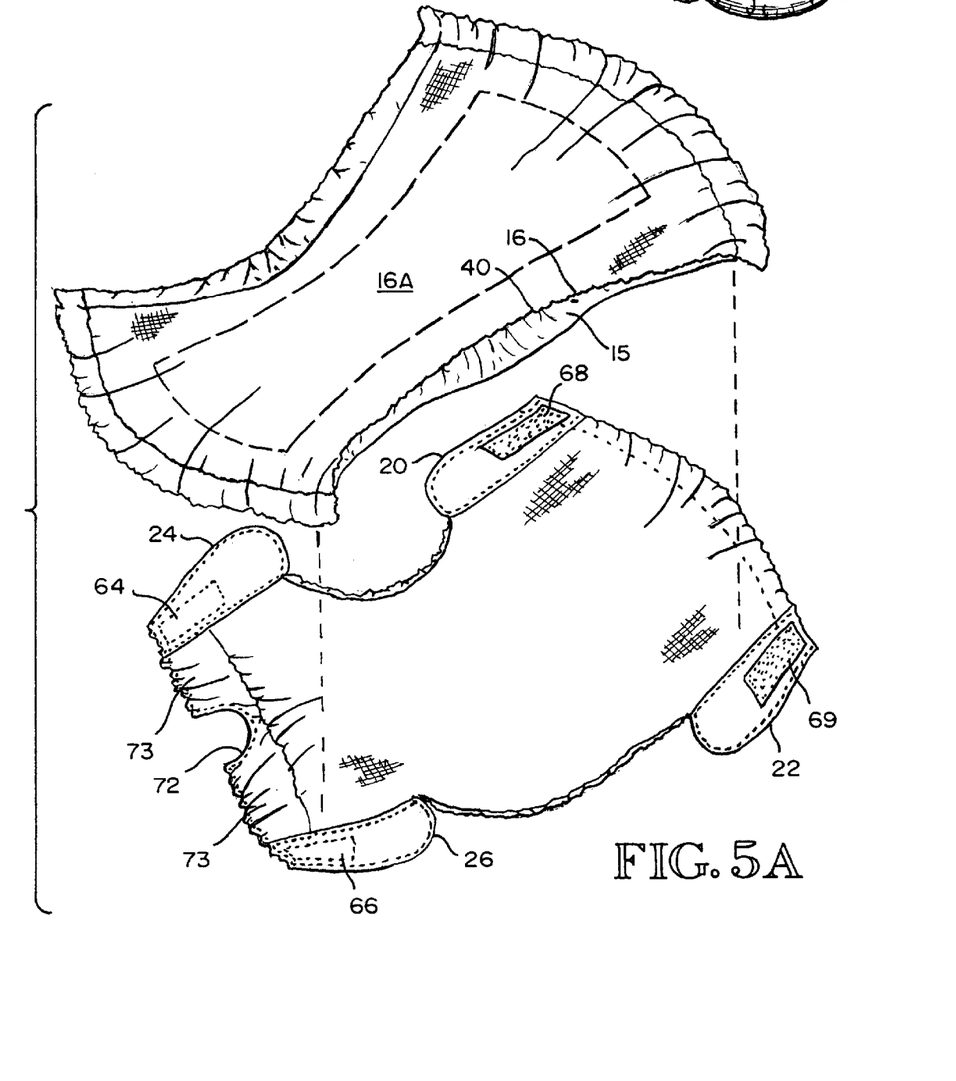
FIG. 5A shows a view of the interior surface of the premature or newborn baby diaper in accordance with the second embodiment of the invention.

A belly button area 72 is left open in the shell 12 for air circulation or medical needs, otherwise the diaper as shown in FIGS. 5, 5A, 5B and 5C is constructed the same as the diaper of FIGS. 1 through 4. The shell in the belly button area 72 now has a U-shape to it as shown in FIG. 5A in which the back of a frontal area 73 is lined with flannel and an elastic is set in under the flannel between the flannel and the frontal area 73 and between the front tabs 24 and 26.

Figure 5B:
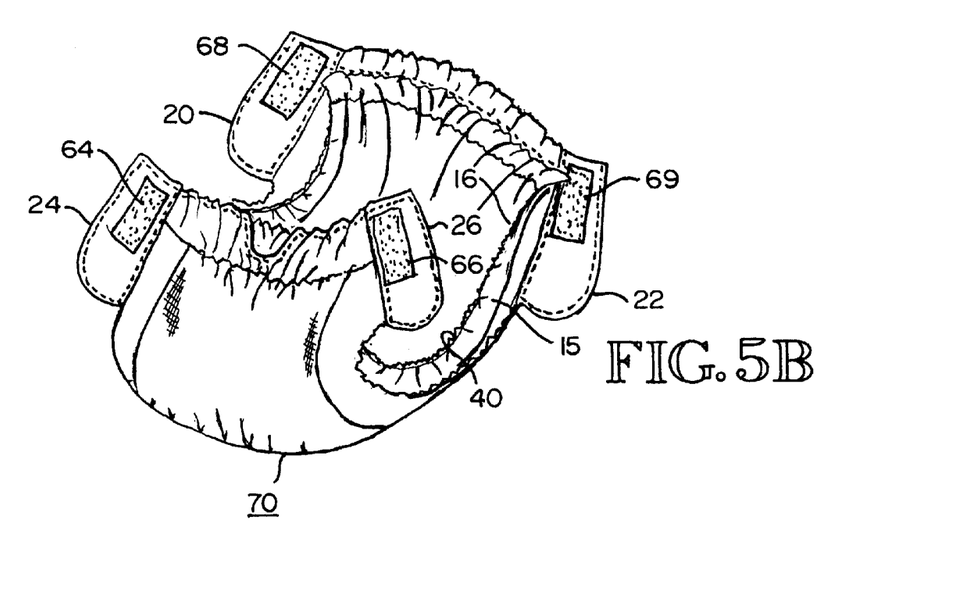
FIG. 5B shows an outside view of the second embodiment of this invention.
Figure 5C:
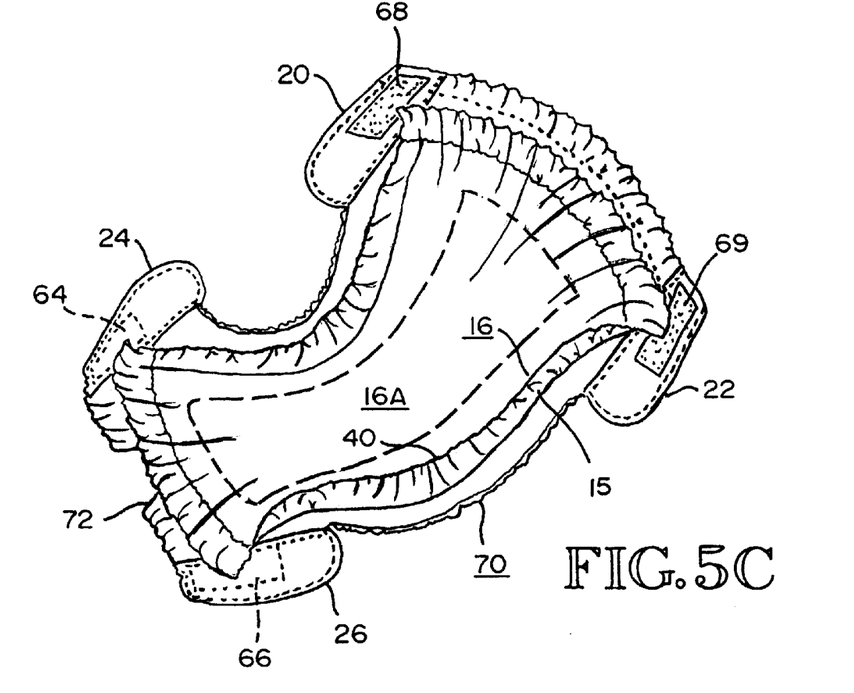
FIG. 5C shows an interior view of the second embodiment of this invention.

FIG. 5B shows an outside view of the second embodiment of this invention FIG. 5C shows the interior of the premature or newborn baby diaper in accordance with the teachings of the second embodiment of this invention.

Figure 6:
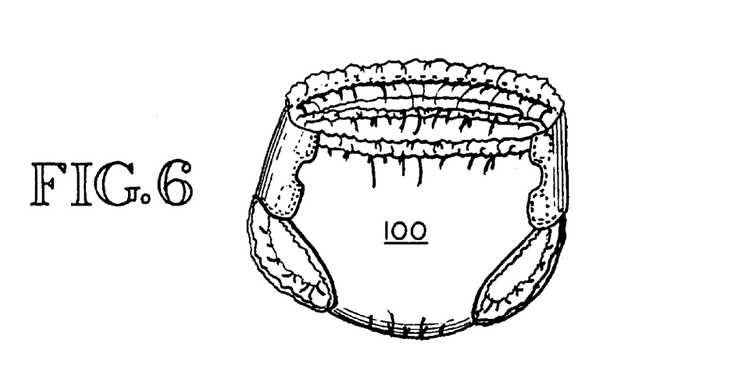
FIG. 6 shows a view of a colostomy diaper in the closed position in accordance with a third embodiment of this invention.

FIG. 6 illustrates a colostomy diaper 100 which represents the third embodiment of this invention with the diaper 100 folded in a position to be worn. This diaper 100 has a liquid impervious bag 102 on the interior frontal portion of the diaper 100 where a colostomy bag on a patient may be inserted in the bag 102 to protect the patient from any leakage from the colostomy bag.

Figure 6A:
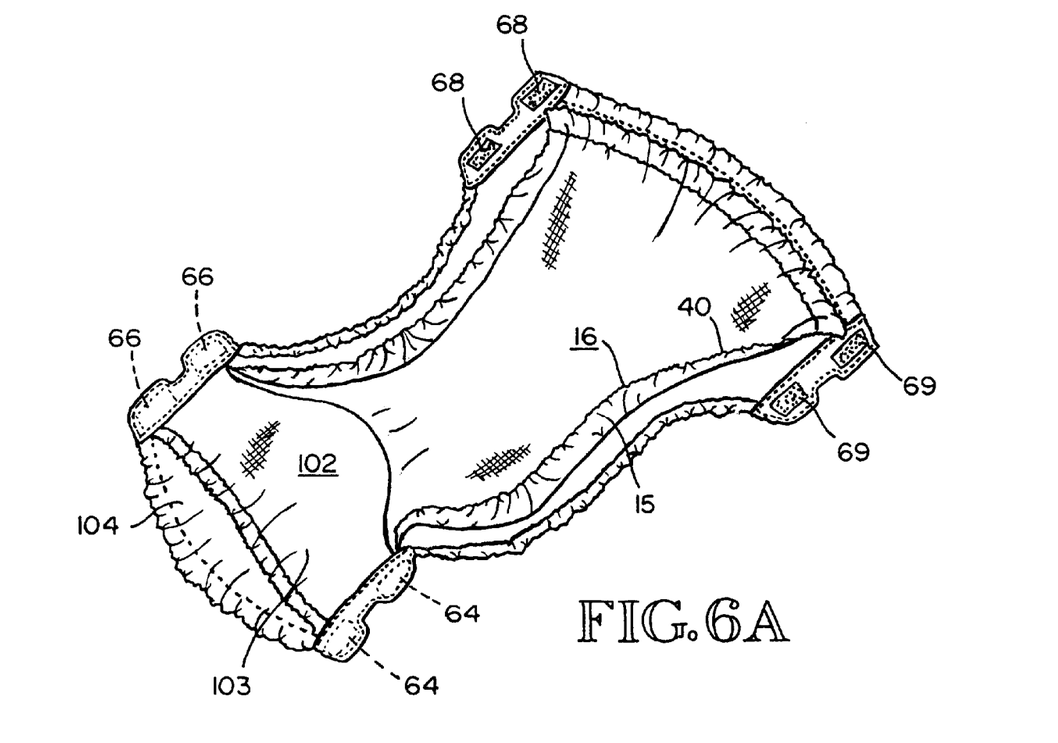
FIG. 6A is an interior surface view of the colostomy diaper in accordance with the third embodiment of this invention.

FIG. 6A shows the interior of the diaper 100 with the bag 102 in the frontal area. The bag 102 and the diaper 100 are constructed in the same way as the diaper 10 in FIGS. 1 through 4, namely with an outer cloth shell 103, an interior liquid impervious layer and last an absorbent section 104 on the interior side of the impervious layer. The top of the bag 102 at the inside is stitched to the top of the front 14 of the shell 12. Owing to the medical need for the unobstructed passage of medical hoses, the VELCRO® hooks 64 and 66 are each in separated tabs, thus permitting the hoses to pass between separated tabs when the diaper 100 is in a position to be worn.

Figure 7:
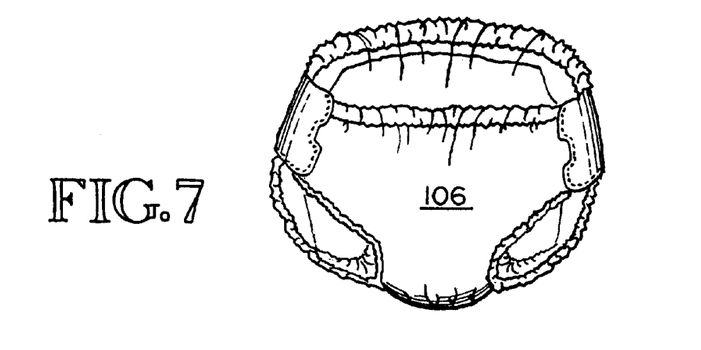
FIG. 7 shows a view of a lighter incontinent diaper in the closed position in accordance with a fourth embodiment of this invention.
Figure 7A:
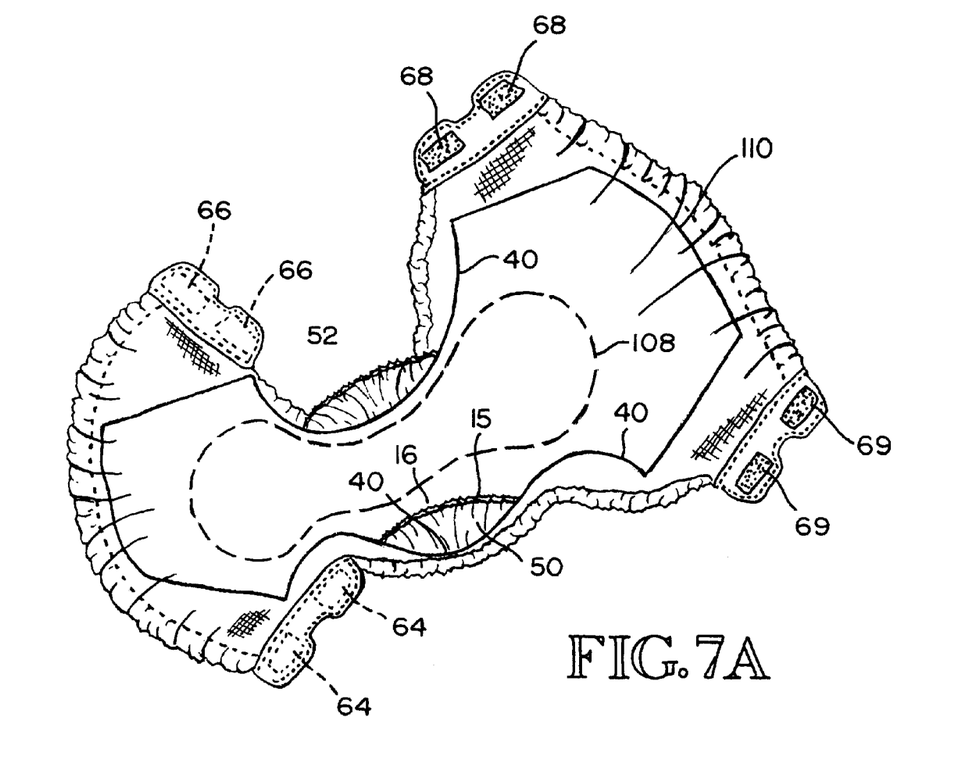
FIG. 7A is an interior surface view of the lighter incontinent diaper in accordance with the fourth embodiment of the invention.

A fourth embodiment of this invention is shown in FIG. 7 and illustrates a lighter incontinent diaper 106 shown in a position to be worn. FIG. 7A shows the interior of this diaper wherein a central portion 108 of absorbent material is substantially smaller, for those who are less incontinent. A pad 110, including the layers of absorbent material has less absorbent material than the preferred embodiment of FIGS. 1 through 4 but the diaper 106 still comprises the same three components of the basic system. The gussets 50 and 52 on the inside of the leg ensure the same leakage protection.

Figure 9A:
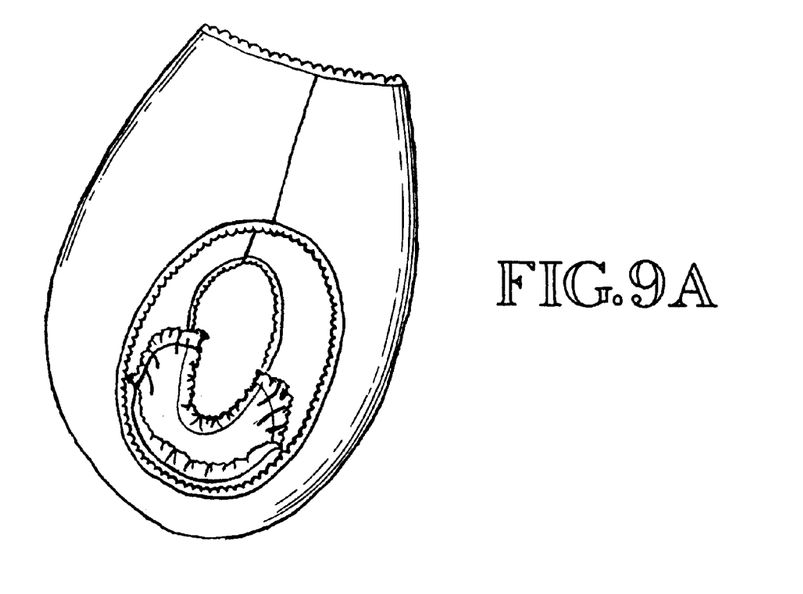

In accordance with the fifth embodiment of this invention the diaper, by eliminating the VELCRO hooks and loops on the preferred embodiment of FIGS. 1 through 4 the diaper is made into a pull-up diaper 114 for boys as shown in FIGS. 8 and 8A and for girls as shown in FIGS. 9 and 9A. As shown and constructed the diapers 114 and 116 are a single unitary structure at the waistband. Inside the diapers 114 and 116 are positioned and anchored the three main components of an assembled pad embodying the teachings of this invention.

The diapers embodying the teachings of this invention have several advantages.

The diaper as a reusable diaper has its components united as one with no pieces to put together. Having an outer shell of non plastic material, the diaper is extremely comfortable and is breathable so that little harm is done to the skin of the wearer. From an adult viewpoint the diaper is not only comfortable but it provides the dignity of little noise on movement of the body. The diaper of this invention also provides good absorption and little or no staining and thus little or no leakage problem. This diaper is also constructed and assembled so as to minimize labor costs. For instance, the shape of the main component parts of the diaper, being basically long sweeping lines, minimize the cutting and stitching time and permit the use of less skilled labor, thus minimizing labor cost. The fact that in cutting out the various components of the diaper there is no need to color match or configurate such things as stripes etc. there are no small pieces to assemble reducing the amount of material that must be used as well as the layout time, thus, minimizing material and labor costs.

I claim as my invention:

1. In a reusable diaper, the combination comprising, an outer liquid permeable shell shaped and constructed to fit a body; a continuous liquid impervious layer; a liquid permeable absorbent material carried by said continuous liquid impervious layer and having a central portion for receiving body waste; and means for permanently attaching the combined said continuous liquid impervious layer and said liquid permeable absorbent material to said outer liquid permeable shell just off each vertical edge of said liquid permeable absorbent material to thus form a leg gusset on both sides of said reusable diaper, with said continuous liquid impervious layer disposed between said outer liquid permeable shell and said liquid permeable absorbent material.

2. In a reusable diaper, the combination comprising, an outer liquid permeable shell shaped and constructed to fit a body; a continuous liquid impervious layer; a liquid permeable absorbent material carried by said continuous liquid impervious layer and having a central portion for receiving body waste; and means for permanently attaching the combined said continuous liquid impervious layer and said liquid permeable absorbent material to said outer liquid permeable shell by stitches along a line just off each vertical edge of said liquid permeable absorbent material to thus form a leg gusset on both sides of said reusable diaper and form an outer covering portion of said outer liquid permeable shell which covers the leg gussets, with said continuous liquid impervious layer disposed between said outer liquid permeable shell and said liquid permeable absorbent material.

3. In a reusable diaper, the combination comprising, an outer liquid permeable shell shaped and constructed to fit a body; a continuous liquid impervious layer; a liquid permeable absorbent material having a first absorbent layer carried by said continuous liquid impervious layer and having a central portion for receiving body waste; means permanently attaching the combined said first layer of said liquid permeable absorbent material and said continuous liquid impervious layer to said outer liquid permeable shell along a line just off each vertical edge of said first layer of said permeable absorbent material to thus form a leg gusset on both sides of said reusable diaper and form an outer covering portion of said outer liquid permeable shell which covers the leg gussets, with said continuous liquid impervious layer disposed between said outer liquid permeable shell and said first layer of said liquid permeable absorbent material; and elastic material stitched along a stitching line just off each horizontal edge of said first layer of said liquid permeable absorbent material for gathering and stitching together said first layer of said liquid permeable absorbent material and said continuous liquid impervious layer.

4. In a reusable diaper, the combination comprising, an outer liquid permeable cloth shell shaped and constructed to fit a body; a continuous liquid impervious layer; a liquid permeable absorbent material having a first absorbent layer carried by said continuous liquid impervious layer and having a central portion for receiving body waste; means permanently attaching, by stitching along a line, the combined said first layer of said liquid permeable absorbent material and said continuous liquid impervious layer to said outer liquid permeable cloth shell just off each vertical edge of said first layer of said permeable absorbent material to thus form a leg gusset on both sides of said reusable diaper and form an outer covering portion of said outer liquid permeable cloth shell which covers the leg gussets, with said liquid impervious layer disposed between said outer liquid permeable cloth shell and said first absorbent layer of said liquid permeable absorbent material; and elastic material stitched along a stitching line just off each horizontal edge of said first absorbent layer of said liquid permeable absorbent material for gathering and stitching together said first absorbent layer of said liquid permeable absorbent material and said continuous liquid impervious layer.

5. In a reusable diaper, the combination comprising, an outer liquid permeable shell shaped and constructed to fit a body; a continuous liquid impervious layer; a liquid permeable absorbent material, having a first absorbent layer of generally the same shape as said continuous liquid impervious layer and having a central portion for receiving body waste; means permanently attaching the combined continuous liquid impervious layer and said first absorbent layer of said liquid permeable absorbent material to said outer liquid permeable shell, just off each vertical edge of said first absorbent layer of said liquid permeable absorbent material, to thus form a leg gusset on both sides of the reusable diaper, with the impervious layer disposed between said liquid permeable shell and said first absorbent layer; elastic means disposed along said vertical edge of said first absorbent layer to thus form fit the leg gussets to the body.

6. In a reusable diaper, the combination comprising, an outer liquid permeable shell shaped and constructed to fit a body; a continuous liquid impervious layer; a liquid permeable absorbent material, having a first absorbent layer of generally the sane shape as said continuous liquid impervious layer and carried by said continuous liquid impervious layer and having a central portion for receiving body waste; means permanently attaching the combined continuous liquid impervious layer and said first absorbent layer of said liquid permeable absorbent material to said outer liquid permeable shell, just off each vertical edge of said first absorbent layer, to thus form a leg gusset on both sides of said reusable diaper, with said continuous liquid impervious layer disposed between said liquid permeable shell and said first absorbent layer; elastic means disposed along said vertical edge of said first absorbent layer to thus fit the leg gussets to the body; and elastic means disposed along a line just off each horizontal edge of the said first absorbent layer of said liquid permeable absorbent material for gathering and attaching together said first absorbent layer of said liquid permeable absorbent material and said continuous liquid impervious layer.

\* \* \* \* \*